(12) United States Patent
Martin

(10) Patent No.: US 8,729,135 B2
(45) Date of Patent: May 20, 2014

(54) GLUTARALDEHYDE COMPOSITION

(76) Inventor: Antonietta Pamela Martin, Parkhurst (ZA)

( * ) Notice: Subject to any disclaimer, the term of this patent is extended or adjusted under 35 U.S.C. 154(b) by 370 days.

(21) Appl. No.: 12/381,573

(22) Filed: Mar. 13, 2009

(65) Prior Publication Data

US 2009/0227684 A1 Sep. 10, 2009

Related U.S. Application Data

(63) Continuation-in-part of application No. 10/485,070, filed as application No. PCT/IB02/02913 on Jul. 26, 2002, now abandoned.

(51) Int. Cl.
*A01N 35/02* (2006.01)
*A61K 31/11* (2006.01)

(52) U.S. Cl.
USPC ........... 514/693; 514/698; 514/705; 514/642; 424/641; 424/76.8; 422/36

(58) Field of Classification Search
USPC ......... 514/698, 705, 693, 642; 424/641, 76.8; 422/36
See application file for complete search history.

(56) References Cited

U.S. PATENT DOCUMENTS

| | | | |
|---|---|---|---|
| 3,912,450 A | 10/1975 | Boucher | |
| 3,968,248 A * | 7/1976 | Boucher | 514/705 |
| 4,093,744 A | 6/1978 | Winicov et al. | |
| 4,880,602 A | 11/1989 | Al-Sioufi | |
| 5,158,778 A | 10/1992 | Donovan et al. | |
| 5,674,829 A | 10/1997 | Martin | |

FOREIGN PATENT DOCUMENTS

| | | |
|---|---|---|
| AU | 689 928 A | 4/1998 |
| EP | 0 609 106 A | 8/1975 |
| EP | 0 836 803 | 4/1998 |
| FR | 2 622 397 A | 5/1989 |
| GB | 1 405 785 A | 9/1975 |
| ZA | 93/0662 | 1/1993 |

OTHER PUBLICATIONS http://www.dow.com/PublishedLiterature/dh_00ae/ 0901b803800aea3b.pdf?filepath=surfactants/pdfs/noreg/119-01950.pdf&fromPage=GetDoc viewed Sep. 23, 2010.*
Co-pending U.S. Appl. No. 10/485,070, filed Jul. 13, 2004.

* cited by examiner

*Primary Examiner* — Savitha Rao
(74) *Attorney, Agent, or Firm* — Pauley Petersen & Erickson

(57) ABSTRACT

This invention relates to a stabilized aqueous glutaraldehyde solution including 0.005% to 45% m/v, suitably 10% to 45% m/v solution of glutaraldehyde, an alcohol ethoxylate non-ionic surfactant, a buffer and a sufficient amount of a pH modifier to bring the pH of the solution to 6.0 to 8.5. The glutaraldehyde and the alcohol ethoxylate non-ionic surfactant are chemically bound together, suitably by complexing. These stable solutions can be stored for a period of at least six months without the glutaraldehyde polymerizing or the pH dropping below 5.0.

20 Claims, 6 Drawing Sheets

US 8,729,135 B2

GLUTARALDEHYDE COMPOSITION

RELATED APPLICATIONS

This application is a continuation-in-part of U.S. patent application Ser. No. 10/485,070, filed on 13 Jul. 2004 now abandoned, the disclosure of which is incorporated by reference, which in turn is a 35 U.S.C. §371 application based on PCT/IB02/02913, filed on 26 Jul. 2002, which in turn claims priority based on New Zealand Patent Application 513,213, filed on 27 Jul. 2001.

BACKGROUND OF THE INVENTION

This invention relates to a glutaraldehyde composition.

Glutaraldehyde in solution is well known as either a cleaning, disinfecting or sterilizing agent. It has been shown to be a powerful external bactericidal, fungicidal and virucidal agent. For glutaraldehyde to be effective as such, however, the pH of the glutaraldehyde solution must be in the range of 7 to 8.5. It is difficult to maintain glutaraldehyde solutions at this pH as they are unstable.

South African Patent No. 93/0662 discloses an aqueous glutaraldehyde solution which comprises 4 to 6% m/v of glutaraldehyde, 19 to 21% m/v nonylphenyl ethoxylate, sufficient of a pH modifier to bring the pH of the solution to 6 to 7.5 and sodium acetate trihydrate in an amount that, with the nonylphenyl ethoxylate, serves to buffer the solution at the specified pH range. Such solutions have been found to be stable for a period of up to six months.

European Patent Application 0,609,106 discloses an aqueous glutaraldehyde solution which may be stable for up to six months. The solution includes an aqueous solution of glutaraldehyde, a non-ionic detergent, sodium acetate, and sufficient pH modifier to bring the solution pH to between 6.0 and 8.5. Nonylphenyl ethoxylate is disclosed as a non-ionic detergent.

It is an object of this invention to provide a new aqueous glutaraldehyde solution.

SUMMARY OF THE INVENTION

According to the invention a stable aqueous glutaraldehyde solution comprises:

a 0.005% to 45% m/v solution of glutaraldehyde (OCH$(CH_2)_3$CHO);

an alcohol ethoxylate non-ionic surfactant;

sodium acetate trihydrate (NaC$_2$H$_3$O$_2$); and sufficient amount of a pH modifier to bring the pH of the solution of 6.0 to 8.5.

By "m/v" it is meant the mass of the solute in grams per 100 ml of the resulting solution, also known as "mas-volume percentage."

By "stable" in relation to the concentrate of the invention, it is meant that the concentrate can be stored for a period of at least six months without the glutaraldehyde polymerising or the pH dropping below 5.0.

A concentrate solution typically comprises 10% to 45% m/v glutaraldehyde and as much sodium acetate trihydrate as is required to buffer the pH of the solution at 6.0 to 8.5, typically about 0.05 to 0.5% m/v sodium acetate trihydrate.

Preferably, the solution contains sufficient pH modifier to bring its pH to 7.5.

The non-ionic surfactant is an alcohol ethoxylate, for example Tergitol®-15S9, is typically at a pH of 8.0 to 9.0, and together with sodium acetate trihydrate, functions as a buffer to maintain the aqueous solution of the invention at the pH of 6 to 8.5. Typically, the alcohol ethoxylate non-ionic surfactant makes up from 0.6 to 25% m/v of the solution. This surfactant is chemically bound to the glutaraldehyde and stabilizes the glutaraldehyde in a more effective linear configuration. The chemical bonding may form a complex between the non-ionic surfactant and glutaraldehyde in which the two compounds are bound together by ionic forces. The alcohol ethoxylate non-ionic surfactant is not a phenyl ethoxylate, and demonstrates improved performance compared to the nonylphenyl ethoxylate disclosed in the above-mentioned publications.

The pH modifier may be a base, for example it may be a dilute aqueous solution of sodium hydroxide (NaOH). It is preferably a 1M aqueous NaOH solution.

The solution may also contain a quaternary ammonium compound (QAC) preferably a twin chain quarternary ammonium compound. Advantageously, the twin chain quaternary compound makes up from 0.1% to 15% m/v of the solution.

A concentrate solution of the invention may be diluted to produce an aqueous sterilising, cleaning, disinfecting, antiseptic, subcutaneous injectable or preservative end use composition, having pH of 5 to 8.5.

Typically, these compositions are formed by diluting a concentrate solution of the invention with sterile or potable water having a pH of 6 to 8.5 to provide a composition of reduced glutaraldehyde concentration.

Preferably, the concentration of glutaraldehyde in these diluted end use compositions is in the range of 0.005% to 5% m/v.

According to another aspect of the invention there is provided a method of producing any one of the stable aqueous glutaraldehyde solutions mentioned above, the method including the steps of:

a) heating water to a temperature between 45° C. to 50° C.;
b) adding an alcohol ethoxylate non-ionic surfactant to the water while maintaining the temperature of the solution so formed between 45° C. to 50° C.;
c) adding a glutaraldehyde solution to the solution;
d) maintaining the temperature of the solution at 45° C. to 50° C. for a period of 15 to 30 minutes to allow the glutaraldehyde to chemically bind, suitably complex with the alcohol ethoxylate non-ionic surfactant;
e) optionally adding other active ingredients to the solution and decreasing the temperature of the solution by adding water to the solution;
f) adjusting the pH of the solution to 7.5 to 8.5 using a pH modifier; and
g) adding sodium acetate trihydrate to the solution to buffer the solution to a pH of 6.0 to 8.5.

The invention also covers a stabilised glutaraldehyde composition having an ESI-HPLC-MS spectrum where the spectral detail is populated in the high mass range (from just below 500 m/z to approximately 900 m/z) of the spectrum, typically a spectral detail substantially the same as that shown in FIG. 4 having a parabolic profile with a homologous series 44 m/z (—CH$_2$—CH$_2$—). The acronym "m/z" refers to "mass-to-charge ratio."

DESCRIPTION OF EMBODIMENTS

The inventor has now developed a new stable concentrate glutaraldehyde solution using a new non-ionic surfactant, namely an alcohol ethoxylate non-ionic surfactant. The inventor has also developed a new concentrate glutaraldehyde solution, the solution having a higher concentration of glutaraldehyde, i.e. the concentrate solution comprises from 10% to 45% m/v of an aqueous solution of glutaraldehyde. Typical concentrate solutions contain 10%, 20%, 30% and 45% m/v glutaraldehyde, depending on the application of the solution.

A concentrate solution contains 0.6 to 0.25% m/v the alcohol ethoxylate non-ionic surfactant (with a pH of 8.0 to 9.0), sodium acetate trihydrate to buffer the pH of the aqueous solution at about 6.0 to 8.5 and sufficient amount of a pH modifier (such as sodium hydroxide) to bring the pH of the aqueous solution up to 6.0 to 8.5, preferably 7.5. Usually the concentrate solution will include about 0.05%-0.5% m/v sodium acetate trihydrate. In addition, the aqueous solution may contain a twin chain quaternary ammonium compound which has increased fungicidal activity of the solution and which also increases the foaming ability of the solution. The increased foaming ability provides a larger surface contact time on application of the product when sprayed onto large surfaces and thus increases the overall efficacy of the product. A twin chain quaternary ammonium compound is used in preference to a single chain of quarternary ammonium compound. The twin chain quaternary ammonium compound has greater steric hinderance to protect the nitrogen atom of the quarternary ammonium compound, making it more stable than glutaraldehyde and a single chain quaternary ammonium compound.

A twin chain quaternary ammonium compound has the formula $R_2$-$N(CH_3)_2Cl^-$ where R represents an alkyl straight chain One preferred example is 1-decanamminium, N-decyl-N,N-dimethyl-chloride.

A glutaraldehyde composition according to the invention is prepared by heating water up to a temperature between 45° C. to 50° C. Sufficient alcohol ethoxylate derivative is added to provide a concentrate containing from 0.6 to 25% m/v of alcohol ethoxylate derivative, while maintaining the temperature of the solution at 45° C. to 50° C. Next, a required amount of glutaraldehyde solution is added to provide a concentrate having a glutaraldehyde concentration of 10 to 45% m/v, while keeping the temperature at 45° C. to 50° C. The glutaraldehyde and detergent are allowed to react, while maintaining the temperature at 45° C. to 50° C. for a period of 15 to 30 minutes. During this time, the glutaraldehyde is chemically bound to the surfactant, and is suitably complexed with the surfactant. Cold water is then added to bring the solution up to 0.75% of the total volume of the concentrate solution.

Figure 1:
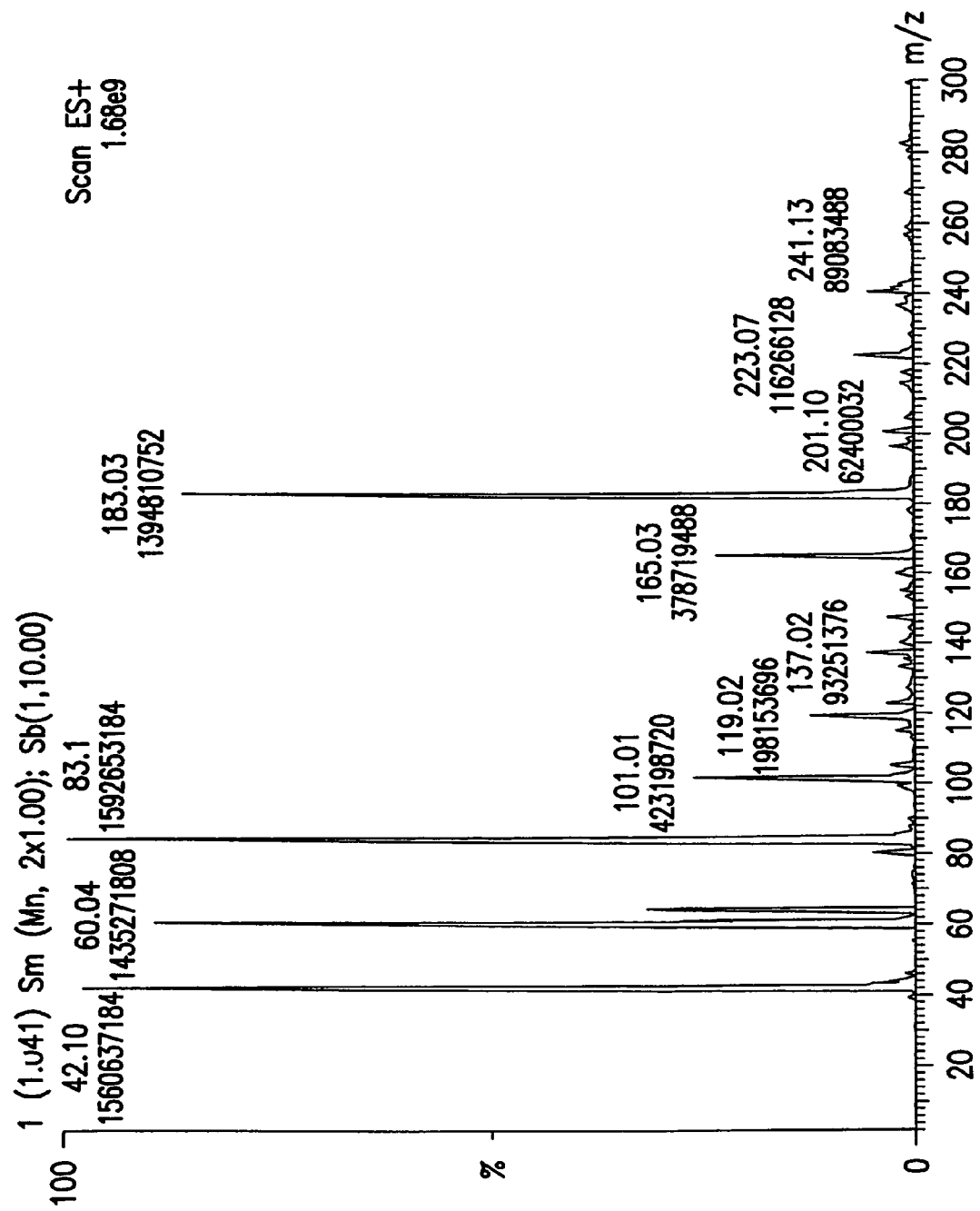
FIG. 1 is an ESI-HPLC-MS spectrum of glutaraldehyde for use in a stabilised glutaraldehyde composition of the invention.
Figure 2:
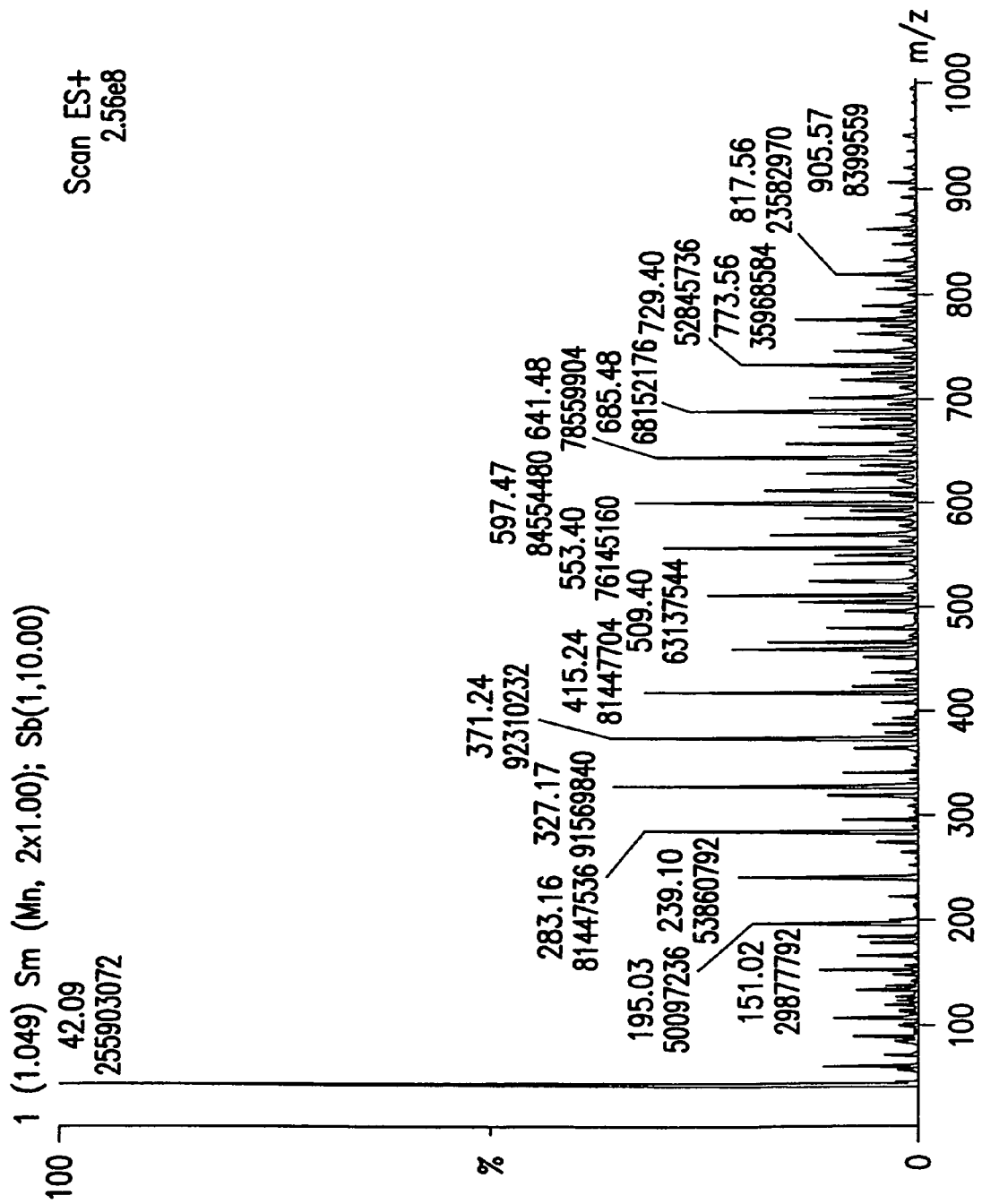
FIG. 2 is an ESI-HPLC-MS spectrum of an alcohol ethoxylated non-ionic surfactant for use in a stabilised glutaraldehyde composition of the invention.
Figure 3:
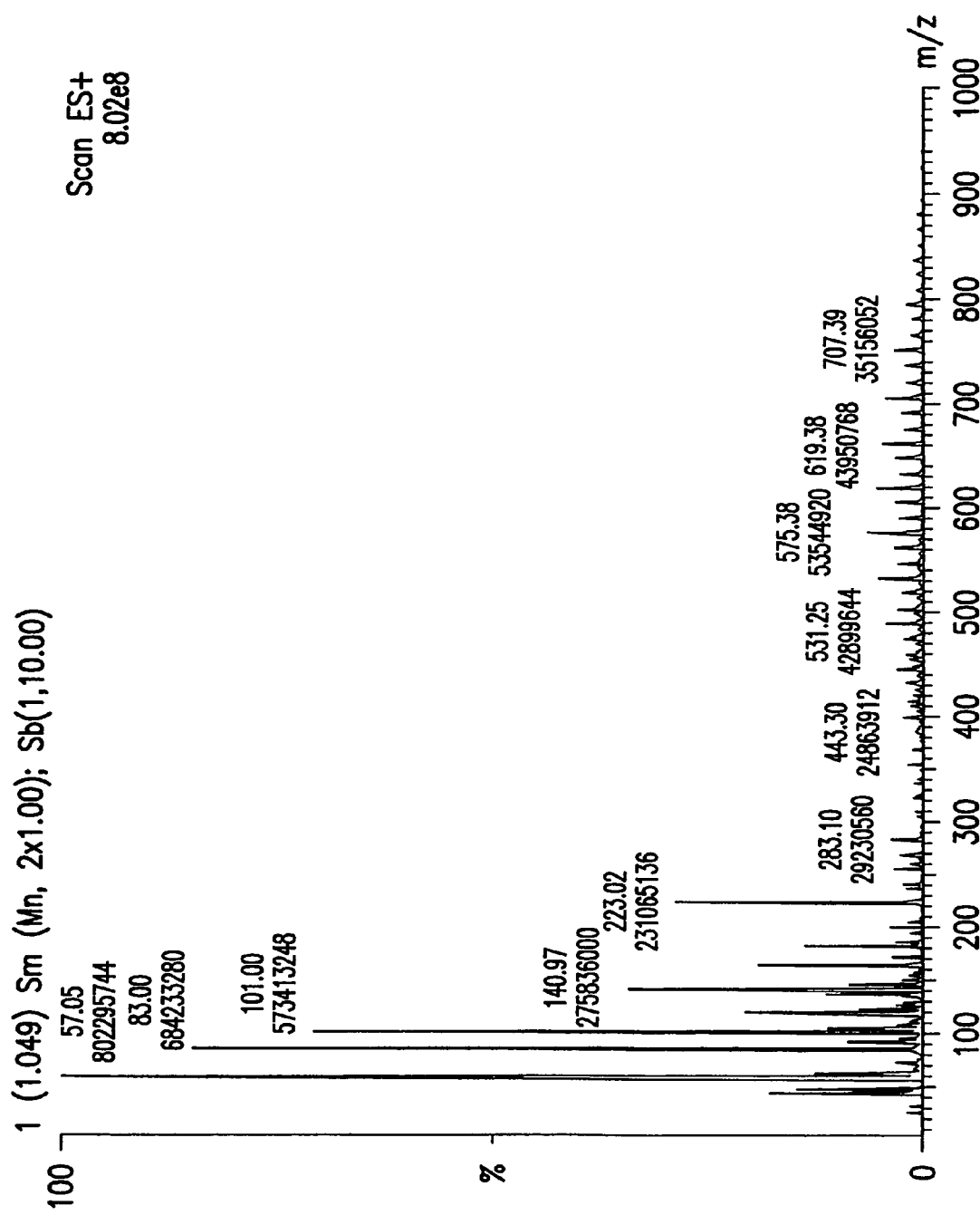
FIG. 3 is an ESI-HPLC-MS spectrum of buffer chemicals (including sodium acetate trihydrate and sodium hydroxide) for use in a stabilised glutaraldehyde composition of the invention.
Figure 4:
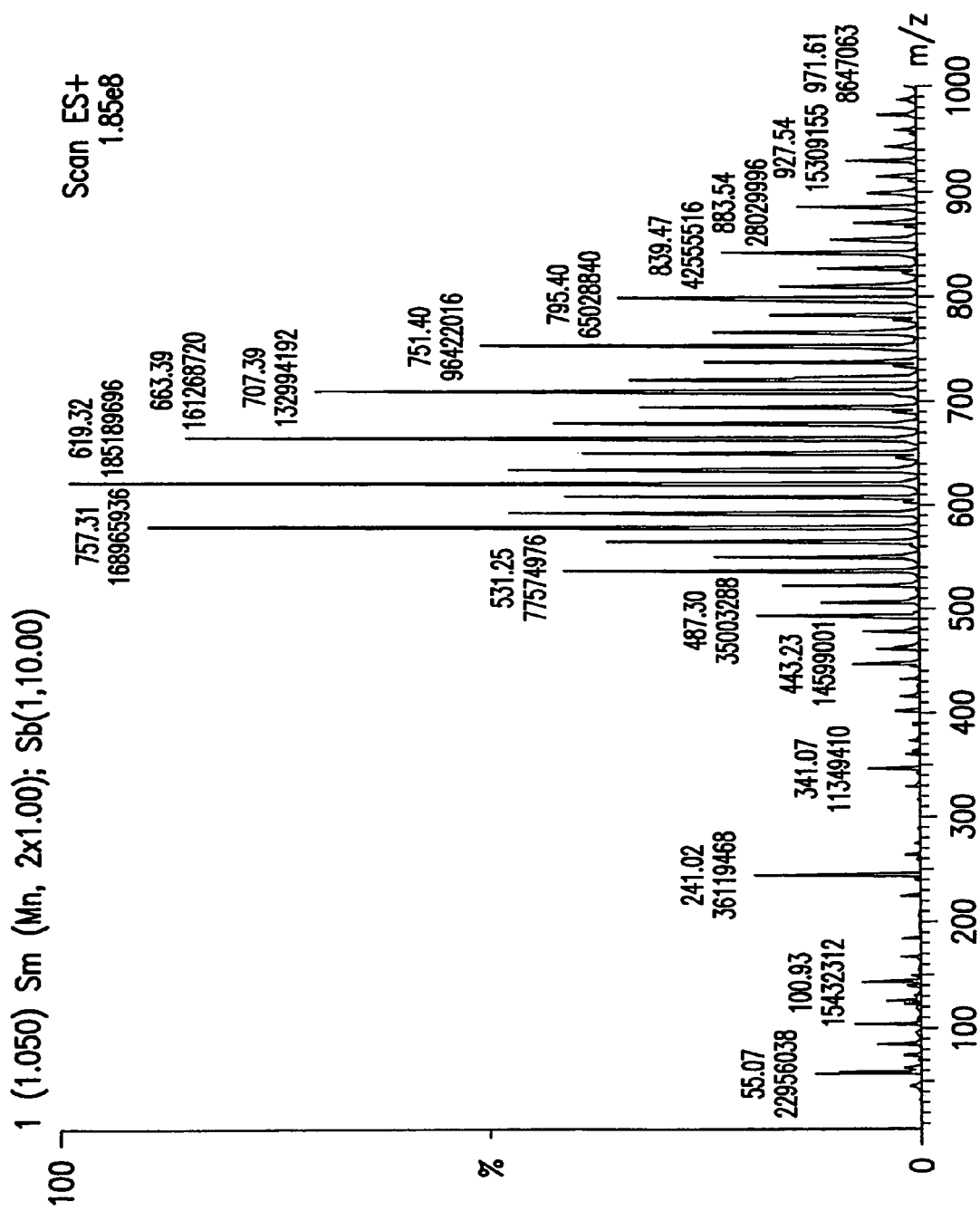
FIG. 4 is an ESI-HPLC-MS spectrum of a stabilised glutaraldehyde composition of the invention.

A comparison of FIG. 4 with FIGS. 1-3 of this specification shows that a new complex is formed between the alcohol ethoxylate non-ionic surfactant and the glutaraldehyde. FIG. 4 is an ESI-HPLC-MS spectrum of a stabilised glutaraldehyde composition of the invention. As explained above, FIGS. 1-3 are ESI-HPLC-MS spectra of the individual ingredients, namely glutaraldehyde (FIG. 1), alcohol ethoxylated non-ionic surfactant (FIG. 2) and buffer chemicals, including sodium acetate trihydrate and sodium hydroxide (FIG. 3).

The complex between the surfactant and the glutaraldehyde is formed by ionic forces between these two compounds and there is no covalent bond. The formation of a complex (which is as a result of the use of the alcohol ethoxylate non-ionic surfactant and the method of the invention and in particular the heating step) results in the glutaraldehyde solution of the invention which has better stability than that disclosed in South African Patent No. 93/0662 or European Patent Application 0,609,106. This is explained further below.

Thereafter, all, some or one of the following ingredients may be added, depending on the application:

a) Sufficient amount of a twin chain quaternary ammonium compound to provide a 0.1%-15% m/v concentration in the concentrate.

b) Sufficient amount of a degreasing additive, for example a glycolic solvent to provide a concentration of 0.5%-2% m/v in the concentrate.

c) Sufficient amount of a glycolic acid to provide a 0.5%-30% m/v concentration in the concentrate.

d) Sufficient amount of sodium lauryl ethyl sulphate to provide a concentration of 5%-20% m/v of the concentrate.

e) Sufficient amount of water soluble silicon products to form a 0.01%-0.2% m/v of the concentrate and to act as a defoamer in certain applications.

After all, or some, or one of the above ingredients is added, the solution is brought up to its final volume with water. Thereafter, the pH of the solution is adjusted to 7.5 to 8.5 with a pH modifier such as sodium hydroxide (typically a 1M aqueous solution). Thereafter, sodium acetate trihydrate is added to buffer the product at a pH of 6.0 to 8.5.

An anti-corrosive inhibitor such as sodium nitrate may then be added, and dyes may be added for aesthetic purposes, and liquid fragrances (that are non-nitrogen based) may also be added.

We refer again to the Figures. It will be seen that the ESI-HPLC-MS spectrum of the stabilised glutaraldehyde composition of the invention, shown in FIG. 4, is very different from the starting materials shown in FIGS. 1-3. In particular, it will be noted that the spectrum for the alcohol ethoxylated non-ionic surfactant has a relatively flat profile with a homogeneous series of 44 m/z (—$CH_2CH_2$—). It would seem that the spectral detail is populated relatively uniformly across the mass range of the spectrum (the low mass range as well as the high mass range) with no region dominating in particular. By comparison, the spectrum for the stabilised glutaraldehyde composition of the invention (i.e. the glutaraldehyde complexed with the alcohol ethoxylate non-ionic surfactant) has the appearance of a parabolic profile with a homologous series of 44 m/z (—$CH_2$—$CH_2$—). The spectral detail is populated at the high mass range (from just below 500 m/z to approximately 900 m/z) of the spectrum with relatively little detail in the low mass region (except for the 241 m/z ion). The highest ions in the given mass spectrum are 575.31 m/z, 619.32 m/z and 663.39 m/z.

The glutaraldehyde solutions described above have a shelf life of a minimum of six months.

In use, the concentrate solution is diluted to provide end use compositions being in the range of 0.001% to 5% m/v glutaraldehyde. When diluted, the end use compositions will typically have a pH of 6 to 8.5 which is the pH at which glutaraldehyde is optimally activated. At this neutral, or close to neutral pH, the solutions are non-corrosive and non-irritant and hence user friendly. Further, the concentrate glutaraldehyde solutions are compatible with products that may be used in end-use compositions, such as: defoamers (e.g. water-soluble synthetic silicon type products); degreasers (e.g. glycols); surfactants (e.g. sodium lauryl ethyl sulphate, triethalamines and cocoamides); thickeners (e.g. cellulose hydroxyls and starch thickeners), pH activators (e.g. citric acid); pesticides (e.g. permethrine) and other products that do not contain non-steric hindered nitrogen elements.

The product can be used in many applications, including in domestic cleaning products, personal hygiene products, as a water preservative, in sewage water purification, in pharmaceutical products as an effective biocide, in preventative medication including disinfecting of needles or washing needles, stabs or pricks etc. It is also useful as a machine cleaner in combination with other chemicals, such as glycolic acid, as an animal skin care washing or dipping products or for the cleaning of food products. The product is also compatible with degreasing chemicals, for example glycols.

End-use compositions made by diluting a concentrate composition according to the invention are set out below:

| End-Use Composition | Percent (%) by Weight Active Glutaraldehyde |
|---|---|
| Medical Instrument Sterilent | 2.0%-3.2% |
| Domestic Household Cleaner | 0.3%-0.5% |
| Toilet Cleaner | 1%-5% |
| Waste Water Treatment | 30%-45% concentrates which are diluted to 0.001%-0.025% when applied to waste water |
| Dairy Machine Cleaner | 0.1%-6% |
| Skin Cleansers and Creams | 0.3%-0.5% |
| Injectables and Skin Preventative Application | 0.005%-0.3% |
| Abattoir Cleaners and Degreasers for all Surfaces | 0.1%-5% |
| Wall and Surface Cleaners for the Poultry Industry | 0.005%-1% |
| Surface Disinfectants for Food Processing Industries | 0.025%-1% |
| Cell Culturing, Planting, Seedling Growing and Watering Systems | 0.05%-0.3% |
| Pesticide and Biocide | 0.025%-1% |
| Wipes and Swabs | 0.1%-0.3% |

EXAMPLES

Example 1

10% m/v Concentrate Solution Glutaraldehyde

The ingredients of a 10% m/v low foam concentrate low foam concentrate solution of glutaraldehyde according to the invention are set out below:
a) 200-226 kg Ucarcide® 250 which includes 50% w/w glutaraldehyde;
b) 6-22 kg Tergitol® 15.S9;
c) 6-50 kg twin chain quaternary ammonium compound (1-decanamminium, N-decyl-N,N-dimethyl-chloride);
d) 2.5 kg-10 kg sodium acetate trihydrate;
e) sufficient sodium hydroxide to bring the pH of the solution to 7.5; and
f) 1-2 kg Dowanol® DPM glycol (degreaser).

The ingredients of a 1000 l 10% m/v high foam concentrate solution of glutaraldehyde are set out below:
a) 200-226 kg Ucarcide® 250 which includes 50% w/w glutaraldehyde;
b) 100-150 g Tergitol® 15.S.9;
c) 6-50 kg twin chain quaternary ammonium compound (1-decanamminium, N-decyl-N,N-dimethyl-chloride);
d) 2.5 kg-10 kg sodium acetate trihydrate;
e) sufficient sodium hydroxide to bring the pH of the solution to 7.5; and
f) 1-2 kg Dowanol® DPM gycol (degreaser).

Example 2

20% m/v Glutaraldehyde Concentrate Composition

The ingredients of a 1000 l 20% m/v glutaraldehyde solution of the invention are as set out below:
a) 400-452 kg Ucarcide® 250 which includes 50% w/w glutaraldehyde;
b) 6-22 kg Tergitol® 15.S.9;
c) 6-50 kg twin chain quaternary ammonium compound (1-decanamminium, N-decyl-N,N-dimethyl-chloride);
d) 5 kg-15 kg sodium acetate trihydrate;
e) sufficient sodium hydroxide to bring the pH of the solution to 7.5; and
f) 1-2 kg Dowanol® DPM glycol (degreaser).

Example 3

30% m/v Glutaraldehyde Concentrate Composition

The ingredients of a 1000 l 30% m/v glutaraldehyde solution of the invention are as set out below:
a) 600-678 kg Ucarcide® 250 which includes 50% w/w glutaraldehyde;
b) 6-22 kg Tergitol® 15.S.9;
c) 6-50 kg twin chain quaternary ammonium compound (1-decanamminium, N-decyl-N,N-dimethyl-chloride);
d) 10 kg-20 kg sodium acetate trihydrate;
e) sufficient sodium hydroxide to bring the pH of the solution to 7.5; and
f) 1-2 kg Dowanol® DPM glycol (degreaser).

Example 4

45% m/v Glutaraldehyde Concentrate Composition

The ingredients of a 1000 l 45% m/v glutaraldehyde solution of the invention are as set out below:
a) 900 kg Ucarcide® 250 which includes 50% w/w glutaraldehyde;
b) 6-22 kg Tergitol® 15.S.9;
c) 6-50 kg twin chain quaternary ammonium compound (1-decanamminium, N-decyl-N,N-dimethyl-chloride);
d) 10 kg-20 kg sodium acetate trihydrate;
e) sufficient sodium hydroxide to bring the pH of the solution to 7.5; and
f) 1-2 kg Dowanol® DPM glycol (degreaser).

Example 5

Effect of Heat on Complexing

This example demonstrates that sufficient heat is needed to obtain a complex between the alcohol ethoxylate non-ionic surfactant and the glutaraldehyde. The following four samples were prepared and compared.
Sample 1: A 10% active glutaraldehyde aqueous solution. The water used was deionized bacteria filtered water.

Sample 2: A 0.98% active Tergitol® 15S9 (alcohol ethoxylated non ionic surfactant) solution. The water used as the diluent was the same as that used for preparing Sample 1.

Sample 3: A 10% stabilised glutaraldehyde solution prepared by the method described above using the heating step. The water used as the diluent was the same as that used for preparing Sample 1.

Sample 4: A 10% stabilised glutaraldehyde solution prepared by the method described above, but without any heating. The water used as the diluent was the same as that used for preparing Sample 1.

Each of the Samples was tested by injecting directly into an electron spray ionization mass spectroscopy. The instrument used, located at Potchestroom University, was an Agilent® 1200LC/Agilent® 6210 Time-of-flight (TOF) mass spectrometer. The diluent and mobile phase used were LC mobile phase: $50/50 H_2O/MeCN + 0.1\%$ formic acid at a flow rate of 0.2 ml/min. The sample size injected was 10 microliters injected directly infused into TOF.

The TOF Machine settings were:
Positive ionization;
Gass temperature 300° C.;
Drying Gas 8 L/min;
Nebuliser 35 PSIG;
VCap 3500V;
Fragmenter 140V;
Skimmer 60V; and
Ref masses: 118.086255 and 922.009798

The TOF system was used in combination with a dual-nebulizer ESI source and an automated calibrant delivery system to continuously introduce low-level reference masses to achieve accurate mass assignments. For the analysis, the drying gas flow was set to 8 L/min, with gas temperature at 300° C.; the nebulizer was set to 35 psig and capillary voltage was −3500V; a fragmentor setting of 140V was used with skimmer 60V; the mass range was set to 100-3500 m/z with transients/scan equal to 10000; and internal reference mass correction was used.

Figure 5:
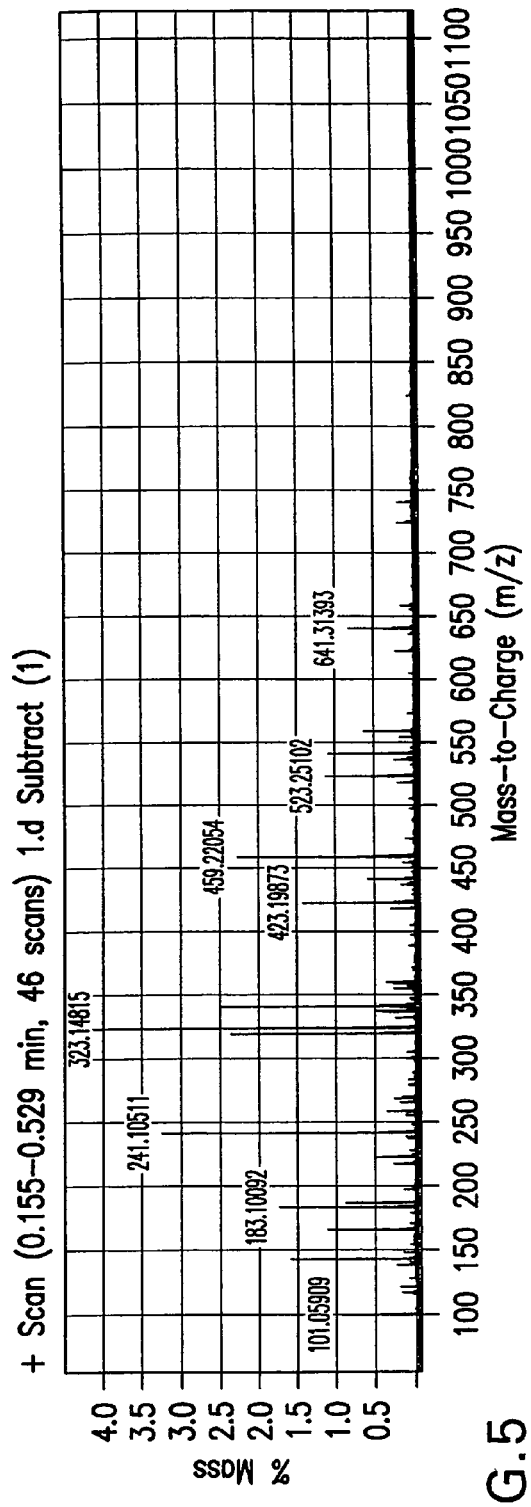
FIGS. 5-8 are electron spray ionization mass spectra of Samples 1-4, respectively, of the compositions described below in Example 5.

FIG. 5 illustrates the results for Sample 1. The glutaraldehyde in solution at 10% exists in different structures and not just one molecular mass. This is expected as it is known that glutaraldehyde can exist in solution as a straight chain, branched chain, and cyclic formats. This is the main reason for its instability. The range of formats is from 100 to 650 m/z.

Figure 6:
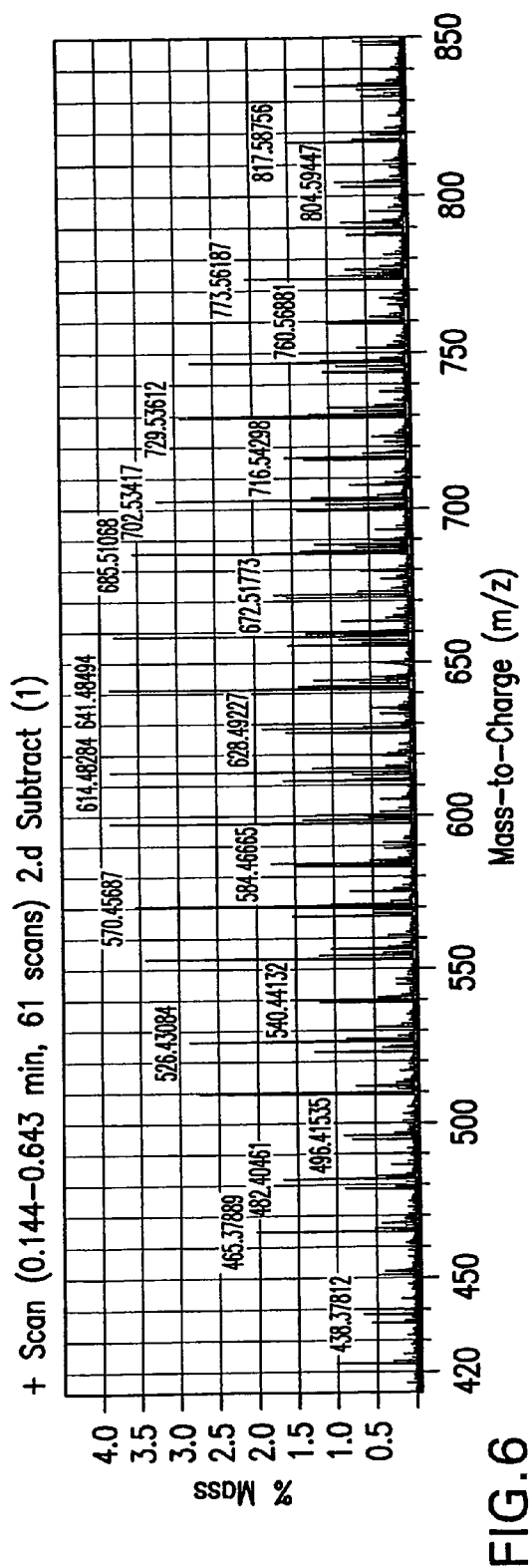

FIG. 6 illustrates the results for Sample 2. Tergitol® 15S9 is a mixture of various chain lengths and ethoxylated by 9 OH groups, hence the many peaks. However, the peaks are in a distinct format and range from 420 to 920 m/z.

Figure 7:
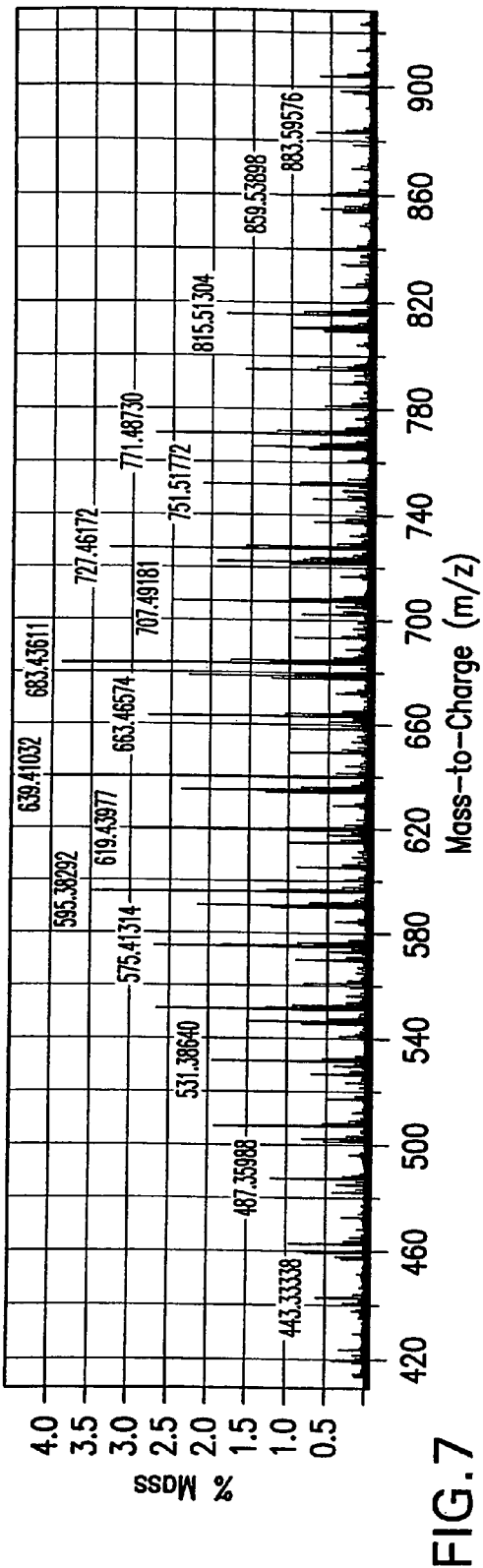

FIG. 7 illustrates the results for Sample 3. No fee glutaraldehyde is seen in this scan as it has all been complexed into the molecular mass of the complex formed. No new compound has been formed, as demonstrated by the shift in the positions of the Tergitol® peaks to the right, which means other chemicals have complexed with it.

Figure 8:
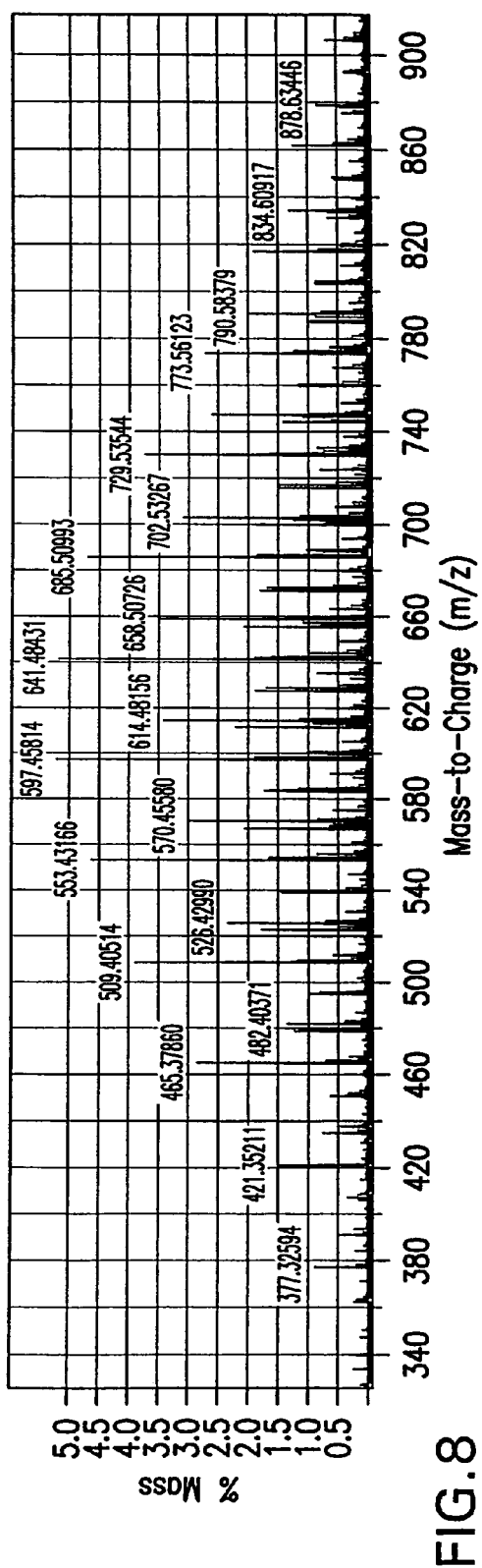

FIG. 8 illustrates the results for Sample 4. Sample 4 was not heated according to Applicant's invention, and thus represents a solution expected by simply mixing the ingredients together. In the unheated mixture of glutaraldehyde and Tergitol® of Sample 4, there is evidence of glutaraldehyde peaks below 420, which is similar to the glutaraldehyde peak on its own. Also, the peaks of the peaks greater than 420 are similar to the Tergitol® scan, and have not shifted to the right. FIG. 4 demonstrates that there is no complex formed, as the two ingredients are separately detectable and simply super-imposed on each other.

I claim:

1. A stable aqueous glutaraldehyde solution comprising the following ingredients:
   a 2% to 45% m/v solution of glutaraldehyde ($OCH(CH_2)_3CHO$);
   an alcohol ethoxylate non-ionic surfactant;
   sodium acetate trihydrate ($NaC_2H_3O_2$); and
   sufficient amount of a pH modifier to bring an initial pH of the solution of 6.0 to 8.5;
   wherein the glutaraldehyde is complexed with the alcohol ethoxylate non-ionic surfactant using heat of at least 45° C. and duration of at least 15 min and the alcohol ethoxylate is not a phenyl ethoxylate, and the ingredients are present in amounts such that the pH of the solution does not fall below 5.0 for at least two years.

2. A concentrate solution according to claim 1 comprising 10% to 45% m/v glutaraldehyde.

3. A solution according to claim 1 comprising as much sodium acetate trihydrate as is required to buffer the pH of the solution at 6.0 to 8.5.

4. A solution according to claim 2 comprising as much sodium trihydrate as is required to buffer the pH of the solution at 6.0 to 8.5.

5. A solution according to claim 4 comprising as much sodium acetate trihydrate as is required to buffer the pH of the solution at 6.0 to 8.5.

6. A solution according to claim 5 comprising about 0.05 to 0.5% m/v sodium acetate trihydrate.

7. A solution according to claim 6 comprising sufficient pH modifier to bring its pH to 7.5.

8. A solution according to claim 6 wherein the alcohol ethoxylate non-ionic surfactant makes up from 0.6 to 25% m/v of the solution.

9. A solution according to claim 6 wherein the pH modifier comprises a dilute aqueous solution of sodium hydroxide.

10. A solution according to claim 6 further comprising a quaternary ammonium compound.

11. A solution according to claim 3 comprising about 0.05 to 0.5% m/v sodium acetate trihydrate.

12. A solution according to claim 1 comprising sufficient pH modifier to bring its pH to 7.5.

13. A solution according to claim 1 wherein the alcohol ethoxylate non-ionic surfactant has a pH of 8.0 to 9.0 and, together with the sodium acetate trihydrate, functions as a buffer to maintain the aqueous solution of the invention at the pH of 6.0 to 8.5.

14. A solution according to claim 13 wherein the alcohol ethoxylate non-ionic surfactant makes up from 0.6 to 25% m/v of the solution.

15. A solution according to claim 1 wherein the pH modifier comprises a dilute aqueous solution of sodium hydroxide.

16. A solution according to claim 15 wherein the pH modifier comprises a 1M aqueous sodium hydroxide solution.

17. A solution according to claim 1 further comprising a quaternary ammonium compound.

18. A solution according to claim 17 wherein the quaternary ammonium compound is a twin chain quaternary ammonium compound.

19. A solution according to claim 18 wherein the twin chain quartemary ammonium compound makes up from 0.1% to 15% m/v of the solution.

20. A method of producing a stable aqueous glutaraldehyde solution comprising the steps of:
   a) heating water to a temperature between 45° C. to 50° C.;
   b) adding an alcohol ethoxylate non-ionic surfactant to the water to form a solution, while maintaining the temperature of the solution so formed between 45° C. to 50° C., wherein the alcohol ethoxylate is not a phenyl ethoxylate;

c) adding a glutaraldehyde to the solution;

d) maintaining the temperature of the solution at 45° C. to 50° C. for a period of 15 to 30 minutes to allow the glutaraldehyde to complex with the non-ionic alcohol ethoxylate surfactant;

e) optionally adding other active ingredients to the solution and decreasing the temperatures of the solution by adding water to the solution;

f) adjusting the pH of the solution to 7.5 to 8.5 using a pH modifier; and g) adding sodium acetate trihydrate to the solution to buffer the solution to a pH of 6.0 to 8.5;

wherein the ingredients are present in amounts such that the pH of the solution does not fall below 5.0 for at least two years.

\* \* \* \* \*